(12) United States Patent
Er et al.

(10) Patent No.: US 10,960,117 B2
(45) Date of Patent: Mar. 30, 2021

(54) CATHETER DEVICE COMPRISING A SEPARATING DEVICE FOR RETAINING MAGNETIC PARTICLES CONTAINED IN A FLUID AND PROTECTION DEVICE FOR A FUNCTIONAL ELEMENT

(71) Applicant: ECP ENTWICKLUNGSGESELLSCHAFT MBH, Berlin (DE)

(72) Inventors: Sami Er, Berlin (DE); Cornelia Simon, Munich (DE); Joerg Schumacher, Teltow (DE); Reiner Liebing, Berlin (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 583 days.

(21) Appl. No.: 15/545,037

(22) PCT Filed: Jan. 22, 2016

(86) PCT No.: PCT/EP2016/051391
§ 371 (c)(1),
(2) Date: Jul. 20, 2017

(87) PCT Pub. No.: WO2016/116630
PCT Pub. Date: Jul. 28, 2016

(65) Prior Publication Data
US 2017/0368305 A1 Dec. 28, 2017

(30) Foreign Application Priority Data

Jan. 22, 2015 (EP) ..................................... 15152201
Jan. 22, 2015 (EP) ..................................... 15152205

(51) Int. Cl.
*A61M 1/10* (2006.01)
*A61M 39/22* (2006.01)
(Continued)

(52) U.S. Cl.
CPC .......... *A61M 1/1087* (2014.02); *A61M 1/102* (2014.02); *A61M 1/1039* (2014.02);
(Continued)

(58) Field of Classification Search
CPC .... A61M 1/101; A61M 1/102; A61M 1/1024; A61M 1/1034; A61M 1/1039;
(Continued)

(56) References Cited

U.S. PATENT DOCUMENTS

| 4,357,237 A | 11/1982 | Sanderson |
| 2004/0055652 A1 | 3/2004 | Erickson |

(Continued)

FOREIGN PATENT DOCUMENTS

| DE | 102010042723 A1 | 4/2012 |
| EP | 0873719 A2 | 10/1998 |

(Continued)

OTHER PUBLICATIONS

International Search Report (PCT/EP2016/051391), dated Sep. 9, 2016.
(Continued)

*Primary Examiner* — Brandy S Lee
(74) *Attorney, Agent, or Firm* — Botos Churchill IP Law LLP

(57) ABSTRACT

A catheter device having a catheter (24) in which a rotating shaft (25) which is made at least partially from a magnetic material is arranged, and a separating device which contains an annular body (27) surrounding the rotating shaft and having a cavity containing a magnetic body (13'), the magnetic body being arranged downstream from a point at
(Continued)

Figure 1:
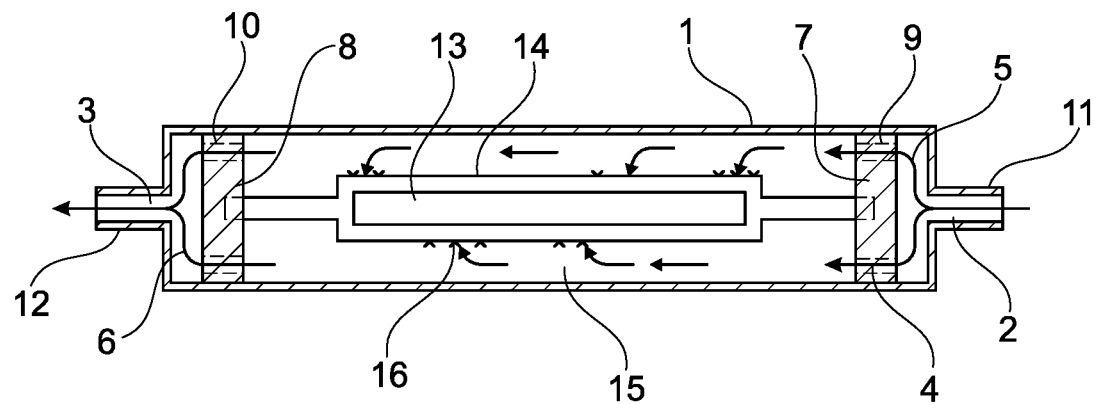

which the shaft (25) exits the catheter (24) which it surrounds with respect to the direction of flow of the fluid through the catheter.

16 Claims, 10 Drawing Sheets

(51) Int. Cl.
*A61M 1/12* (2006.01)
*A61M 25/00* (2006.01)

(52) U.S. Cl.
CPC ............ *A61M 1/122* (2014.02); *A61M 1/125* (2014.02); *A61M 25/0043* (2013.01); *A61M 39/22* (2013.01); *A61M 39/223* (2013.01); *A61M 1/101* (2013.01); *A61M 1/1024* (2014.02); *A61M 1/1034* (2014.02); *A61M 2039/224* (2013.01); *A61M 2039/226* (2013.01); *A61M 2205/0272* (2013.01); *A61M 2205/7545* (2013.01)

(58) Field of Classification Search
CPC .... A61M 1/1087; A61M 1/122; A61M 1/125; A61M 2039/224; A61M 2039/226; A61M 2205/0272; A61M 2205/7545; A61M 25/0043; A61M 39/22; A61M 39/223; A61M 1/1029; A61M 2025/0019; A61M 25/003; F16K 31/0651; F16K 31/0655; F16K 31/0672; F16K 31/0679; F16K 31/0682
See application file for complete search history.

(56) References Cited

U.S. PATENT DOCUMENTS

| | | |
|---|---|---|
| 2004/0153109 A1 | 8/2004 | Tiedtke et al. |
| 2009/0149950 A1 | 6/2009 | Wampler |
| 2010/0331753 A1 | 12/2010 | Gandini |
| 2011/0282274 A1* | 11/2011 | Fulton, III ....... A61B 17/12168 604/28 |
| 2012/0093628 A1* | 4/2012 | Liebing ............... A61M 1/1024 415/1 |
| 2012/0101455 A1 | 4/2012 | Liebing |
| 2012/0145641 A1 | 6/2012 | Rebo et al. |
| 2014/0083948 A1 | 3/2014 | Yang |
| 2014/0261717 A1 | 9/2014 | Egley et al. |
| 2014/0263077 A1 | 9/2014 | Lombardi et al. |

FOREIGN PATENT DOCUMENTS

| | | |
|---|---|---|
| EP | 2047872 A1 | 4/2009 |
| EP | 2246078 A1 | 11/2010 |
| EP | 2 422 735 A1 | 2/2012 |
| WO | 2008/101352 A1 | 8/2008 |

OTHER PUBLICATIONS

Second Office Action for CN Application No. 201680006882 dated Mar. 4, 2020.

* cited by examiner

CATHETER DEVICE COMPRISING A SEPARATING DEVICE FOR RETAINING MAGNETIC PARTICLES CONTAINED IN A FLUID AND PROTECTION DEVICE FOR A FUNCTIONAL ELEMENT

CROSS-REFERENCE TO RELATED APPLICATIONS

This application is a United States National Stage filing under 35 U.S.C. § 371 of International Application No. PCT/EP2016/051391, filed Jan. 22, 2016, which claims the benefit of European Patent Application No. 15152205.9, filed Jan. 22, 2015, and European Patent Application No. 15152201.8, filed Jan. 22, 2015, the contents of all of which are incorporated by reference herein in their entirety.

The invention lies in the field of engineering and mechanics, as well as fluid technology and can be particularly advantageously applied to medical technology for example. Specifically, the invention relates to the separation of magnetic particles from a fluid, in particular from a liquid.

When transporting fluids through flow channels, it is generally not desirable for particles which arise on account of wear for example or which get into the fluid circulation in another manner, to be transported with the moved fluid. Transported particles usually have no use and merely entail risks, for example by way of them getting into moved parts such as ball bearings, plain bearings, motors or rotors, and there, at the minimum causing further wear, or braking or preventing movements due to the increased friction. This is of even more significance if the moved fluid quantities are small, and the movement speed of the fluid is slow, for example as is the case with the rinsing agent circulation in catheters where usually only millilitres are moved in minutes. Moving parts which are applied in the context of medical catheters are usually very sensitive, in the case that undesired particles get into them.

In some cases, undesired particles can be filtered out of the fluid flow by mechanical filters, for example woven fabrics, but this generally entails an increase of the flow resistance.

It is particularly the case with those catheters which lead a rapidly rotating shaft for the drive of functional elements such as blood pumps or blood vessel millers for example, that the wear debris of the shaft material causes negative effects over the course of time. Such shafts general consist of twisted strands, wherein an increased wear and tear arises, in particular when leading such a shaft in an arcuate manner and at high speeds, due to the flexure work.

Magnetic filters are basically already known for holding back magnetic particles. However, these are usually too large for the flow rates of a few millilitres per second and are moreover not suitable for application with saline solutions or other aggressive fluids. Membrane filters usually represent a conduit resistance which is far too high, and are moreover too large and expensive to be used for example as disposable filters. Moreover, membrane filters and in particular the particle quantity which collects in these can significantly compromise the functioning of a flexible shaft for example, which can even lead to the destruction of the flexible shaft.

Against this background of the state of the art, it is the object of the present application of protective rights, to create a protective device or a catheter device or a catheter system or a separating device, which permits magnetic particles to be held back from a fluid flow, without inhibiting the fluid flow or slowing it down, wherein the separating device should also be configured to withstand aggressive fluids.

This object is achieved by the features of the independent patent claims.

The present protective property right application, apart from relating to a separating device, also relates to a catheter device with a catheter, in which a rotating shaft consisting at least partly of a magnetic material is arranged, and with a separating device which comprises a ring body, said ring body surrounding the rotating shaft and being with a cavity containing a magnet body, wherein the magnet body with regard to the flow direction of the fluid through the catheter is arranged downstream of a location, at which the shaft exits out of the catheter surrounding it.

It is clear by way of this, that the separating device with a corresponding catheter device can be applied particularly in the case, in which the wear debris of a rotating shaft within the fluid flow must be separated. For example, such catheters in medical devices are used with rapidly rotating shafts for the drive of functional elements such as millers for blood vessels or heart pumps, so that the occurring wear debris of the shaft material is harmful to the very finely and exactly, but also sensitively constructed functional elements, for example to corresponding plain bearings. It is particularly in this context that it is therefore important to capture the wear debris of the shaft usually consisting of twisted strands of an iron alloy or cobalt alloy.

It is to be emphasised that all separating devices which are disclosed in this protective right application, be they according to the aspects attached at the end of the description, be they according to the embodiments of the patent claims or according to the examples of the figures, as a whole taken per se, can serve as a separating device in a catheter device according to the invention.

Moreover, a part of a respective catheter device according to this protective right application can also be a catheter device with at least one valve for the control of the fluid flow through the catheter, wherein the valve comprises: a valve control space, in which a feed channel runs out with a feed opening and a discharge channel runs out with a discharge opening, and a closure element which is movable in a controlled manner in the valve control space and which in at least one first position closes the discharge opening and, in at least one second position closes the feed opening and which in at least one third position holds open a connection channel between the feed opening and the discharge opening, wherein a valve drive is provided, which selectively moves the closure element at least into the first, second or third position.

It is possible by way of a suitable control or this valve, to give the fluid flow through the transport channel the desired direction. Speeds of fluids or differential speeds through the transport channel can be set for example, up to a direction reversal of the fluid, and this can be usefully applied for example with rinsing procedures.

Examples of such a valve control and fluid leading are explained for example in the parallel ECP 45 PCT (file number not yet known) of ECP GmbH which has been filed on the same day. The priority of the two prior applications EP15152201.8 and EP15152205.9 is moreover claimed. The contents of the closure of all three patent applications in their initially filed form is incorporated by reference in their entirely as a constituent of the present application ("incorporation by reference").

A further development envisages the transport channel comprising a cavity and/or a reservoir for the intermediate storage of particles. Hereby, it is advantageous that the cross section of the transport channel is not reduced in size due to the accumulation of particles. Hereby, the cavity and/or the reservoir is/are to be designed such that the binding of particles is magnetically influenced by way of the influence of the magnet, such that the respective particles at least partly, preferably predominantly or all particles, remain in the cavity or the reservoir.

A further development envisages the cavity and/or the reservoir having two ends, wherein both ends are connected in a fluid-leading manner to the transport channel. The cavity and/or the reservoir for example have a U-shape, in which the particles can collect ("diversion channel"). Alternatively, it is also possible for the cavity and/or the reservoir to have only one branching to the transport channel, for example corresponding to a "railway siding". Characteristic of both these above mentioned variants is the fact that the flow through the transport channel is not disturbed and that above all additional storage volume for the wear debris is provided. In particular no wear debris which is accommodated in the reservoir and/or the cavity should be torn away again and added to the fluid flow through the transport channel, on account of the flowing in the transport channel.

A further advantageous development envisages the reservoir and/or the cavity being designed as a spatially delimited (i.e. limited to a certain flow length) cross-sectional enlargement of the transport channel.

The present protective right application moreover relates to a protective device for a functional element. Such a functional element in particular can be a seal or a bearing (in particular a ball bearing, a plain bearing, a needle bearing or likewise). Moreover, a particularly delicate part of the human or animal body, from which wear debris is to be kept away, can also be considered as a functional element.

The present solution is advantageous since the capture of magnetic wear debris in the case of a complex catheter device represents an effective option for avoiding the entry of magnetic wear debris into the body. This is not predicable or obvious without further ado, since catheter devices until now have often have been directed to the complete avoidance of wear debris by way of a suitable selection of material, coatings and/or geometries, or, due to a suitable limitation of parameters (limitation of rotational speed etc.) had to envisage a compromising of the function, or, by way of a complex leading of the rinsing solution through the multi-lumen catheter, one has attempted to achieve a return of the particles out of the patient, whereby none of these options is in the position of avoiding the entry of wear debris of the most distal bearing into the patient.

Amongst other things, a separating device for holding back magnetic particles located in a fluid is disclosed, wherein this separating device is with a transport channel, in which the fluid can be moved in a throughflow direction, and is with a magnet device, wherein the magnet device comprises at least one magnet which is separated from the fluid by a magnetically permeable solid matter layer. The magnet can advantageously be completely isolated from the fluid by the solid matter layer, in particular can be surrounded by the solid matter layer on all sides.

The magnet device of the separating device for example can comprise one or more permanent magnets or one or more electromagnets or a mixture of both, and the application of a magnetic field ensures that when the fluid flows through the transport channel, the magnetic particles, thus for example iron particles which can be magnetised or non-magnetised, in the proximity of the magnet remain clinging on the inner wall of a flow channel/fluid channel or directly on the solid matter layer of the magnet. Thereby, the flow of the fluid through the transport channel or the fluid channel is not inhibited. Moreover, by way of the separation of the magnet/magnets from the actual fluid, it is ensured that the material of the magnet is itself not damaged, even with a high chemical or physical aggressivity of the fluid, for example with the use of a saline solution, and with non-medical applications even with the use of acids or hot fluids.

An electromagnet for example can be switched of, or a permanent magnet can be temporarily removed from the transport channel, for rinsing the separating device. This has the advantage that the rinsing of the separating device is possible without a removal of the separating device itself from the transport channel.

One design can envisage the magnet interacting exclusively with magnetic or magnetisable particles in the fluid in the transport channel.

The magnet of the separating device in particular is also provided separately of the additional magnet or armature of a pump drive and/or of a valve drive, which can be provided adjacently to the separating device, in particular downstream of the separating device with respect to the preferred flow direction of the fluid.

One design envisages the separating device comprising a first and a second fluid connection, between which the separating device forms a fluid-tight fluid channel.

In this case, a fluid channel, in which the fluid, thus a liquid for example is moved between a first and a second fluid connection, thus for example between a feed channel and a discharge channel is formed within the transport channel directly within the framework of the separating device. The fluid channel in this case can form the transport channel or be formed within the transport channel, for example in the form of a catheter.

A further design envisages a magnet which is encased by a magnetically permeable solid mater layer and around which the fluid can flow at least in regions, in one embodiment for example also on all sides, being arranged in the fluid channel.

In this case, the magnet is arranged within the fluid channel and can provide the fluid flowing past with a maximal interaction surface. Thereby, a suitable widening of the cross section of the fluid channel is advantageous, so that there is enough space for the fluid to be able to flow past the magnet on all sides. The magnet itself can be covered for example with a plastic layer or also with an adequately surface-finished metallisation, on all sides, or at least on the sides which are subjected to the fluid. The magnet should be held with its encasing, for example by way of struts or another holding device, within the fluid channel.

Thereby, it can be advantageous for the magnet to be designed as a cylinder or cuboid, whose length in the longitudinal direction of the fluid channel is greater than its diameter in the transverse direction of the fluid channel and which is arranged in a cylindrical section of the fluid channel.

In this case, the cylindrical or, in cross section rectangular section of the fluid channel as well as the magnet can be designed in an elongate manner, so that adequate interactive times result for the fluid flowing past the magnet, in order to attract the respective magnetic particles to the magnet and for them to be firmly held there.

One can moreover advantageously envisage the magnetic field lines within the magnet running transversely, in particular perpendicularly to the flow direction of the fluid.

In this case, a magnet pole which firmly holds the respective magnetic parts is formed in each case on the sides of the magnet, past which the fluid flows in the longitudinal direction of the fluid channel. The magnetisation can however also be designed in a manner such that the magnet poles are aligned in the longitudinal direction of the fluid channel. The main interactive surface of the magnet with the magnetic particles in the fluid then results at the two ends of the magnet which are situated upstream and downstream.

The separating device can also be designed in a manner such that the magnet, in the flow direction has a lower extension than perpendicular to the flow direction.

In this case, the magnet can form a disc shape, wherein the magnetic disc is set perpendicularly to the fluid direction in the fluid channel and as the case may be produces eddies of the fluid flowing around the disc. In this case, a certain flow resistance is given by the magnet, but due to the eddying of the fluid, one succeeds in all particles located on the fluid, on the path which the cover, sooner or later getting into the direct vicinity of the magnet and being able to be firmly held there.

In the case of an elongate magnet, eddying elements which are stationary in the fluid flow and which ensure a non-laminar flow and ensure that the particles come close to the magnet device can be provided in the region of the separating device.

A further advantageous design for example envisages a ring body surrounding the transport channel, wherein the transport channel is configured for receiving a catheter with a throughflow channel, and wherein a magnet is arranged in the ring body in a cavity situated next to the transport channel.

In this case, the separating device itself does not come into direct contact with the fluid, but the transport channel is configured in a manner such that it can receive a catheter with a fluid channel. This has the advantage that the separating device can be set up and disassembled, without an interruption of the fluid channel, thus for example without an interruption of the fluid flow. One can envisage the ring body being designed as one piece in the peripheral direction for this. However, one can also envisage the ring body being interrupted at least once in the peripheral direction and in particularly being able to be folded open for sticking onto a catheter.

In this case, the application and setting up of the separating device on a catheter is possible in a particularly simple manner, by way of the separating device with the ring body being simply folded open and pushed onto the catheter. The removal of the separating device is also accordingly simple. With this constructional form however, the constructional size of the separating device can increase somewhat compared to a separating device which comprises a magnet which is located in the fluid channel.

A further design envisages the flow channel in the region of the magnet device having a larger cross section than in a region which is arranged upstream of the region of the magnet device in the direction of the fluid.

With this construction, the fluid flow in the region of the separating device is slowed down by the enlarged cross section, so that the magnetic particles can be attracted to the magnet and firmly held, to a greater probability, irrespective of whether the separating device comprises a ring body which surrounds the transport channel and which is with a magnet, or a magnet which itself is located in the fluid channel. Moreover, it is ensured in this manner that the fluid channel is not blocked which is to say that the fluid flow is not inhibited, by the separated particles. The cross section of the fluid channel directly upstream of the separating device, but however also alternatively or additionally directly downstream of the separating device can be reduced compared to the region of the separating device. Thereby, the cross section in the region of the separating device for example can be at least twice, in particular at least thrice or five times the size as directly upstream of the separating device, and for example also be at last twice, thrice or five times as large as directly downstream of the separating device, in the flow direction of the fluid. The fluid channel however can also be designed such that the magnet conveys the particles into a cavity or a reservoir, so that these do not inhibit the fluid flow.

Apart from a separating device of the type described above, as well as a catheter device, the present protective right application further relates to a protective device for a functional element which is in connection with a flowing fluid, wherein a separating device for holding back particles located in the fluid and with at least one magnet element, in particular a separating device of the type described above, is provided along the a flow channel for the fluid, in particular a catheter, in a manner distanced to the functional element and in particular separated from this.

The separating device can advantageously be provided upstream of the functional element with respect to the predominant flow direction of the fluid, but the two mentioned elements can also be simply provided one after the other, in particular distanced to one another, for example also constructionally separated from one another, for example in the form of two separate construction elements with different housings.

The functional element can be free of magnetic or magnetically acting elements and for example be non-magnetic as a whole. It can comprise one or more ball bearings and/or plain bearings. The functional element can for example also comprise a sealing surface which is to be protected from particles.

The functional element can also be something different, particularly something in need of protection, for example a part of a human or animal body. However, in most cases the functional element however is a bearing, e.g. a plain bearing or a ball bearing, and/or a seal.

The functional element can also comprise magnetic components, such as a drive magnet of a rotor for example, or of a translatory drive, or a drive magnet of a magnet valve. The magnet element of the separating device can be a magnet which is separated from the magnetic components of the functional element, or a functional surface of a magnetic construction element which exclusively has the function of particle separation, wherein other functional surfaces of the magnetic construction elements can carry out other functions of the functional element, such as a drive function for example. In the latter case, the magnet element of the separating device can be combined with a magnetic construction element of the functional element, joined together with this, grouped together with this and in particular grouped together with this in housing. The functional surface of the separating device can thus capture and bind particles, in particular magnetic and/or magnetisable particles, before they can get to the functional element.

An additional aspect relates to a functional element which is connected to a separating device, in particular according to the present protective right application, in particular a valve which comprises a closure element which can be driven between two end positions, wherein one or more armatures of a magnetic or magnetisable material or of a material with a particularly low magnetic resistance is/are integrated into the closure element, and wherein a magnet of the separating device is combined with the closure element, in particular is fixedly connected to this, advantageously is co-integrated into this.

The invention is hereinafter represented and explained by way of embodiment examples in figures of a drawing.

Figure 2:
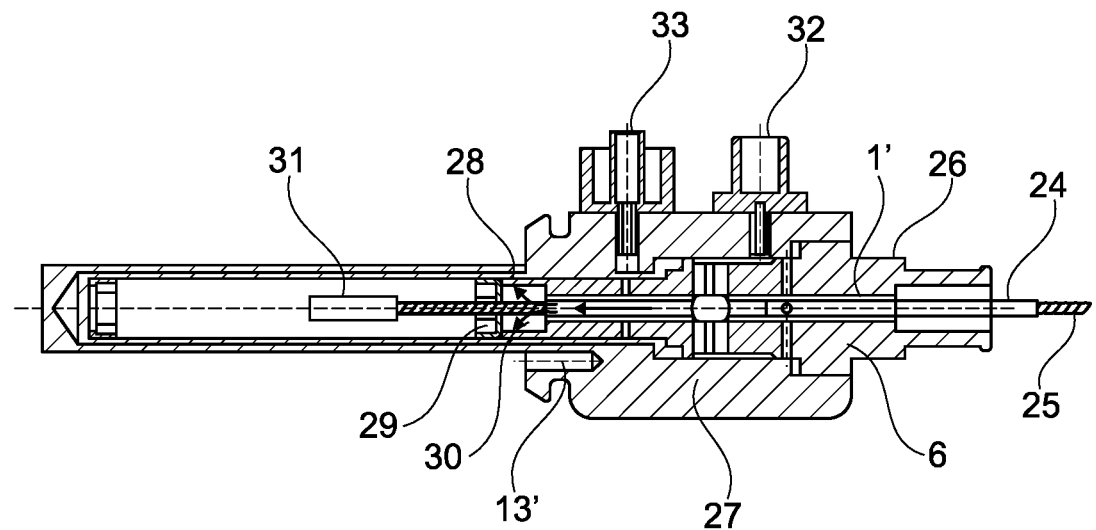
Figure 3:
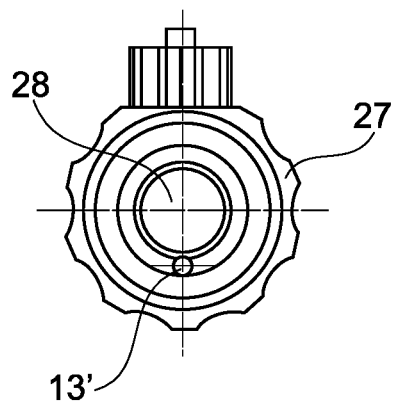
Figure 4:
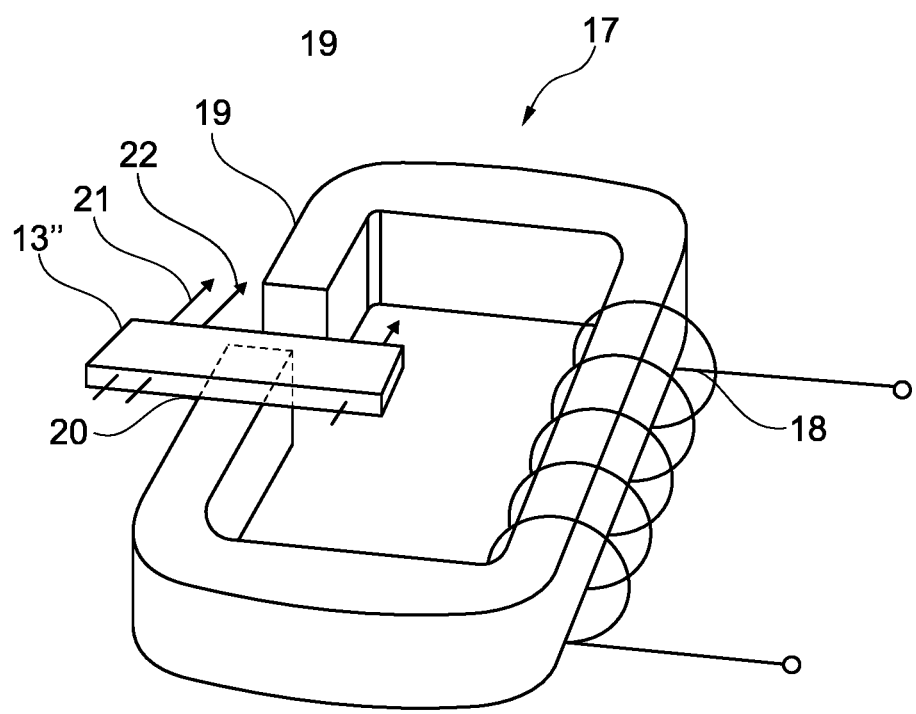
Figure 5:
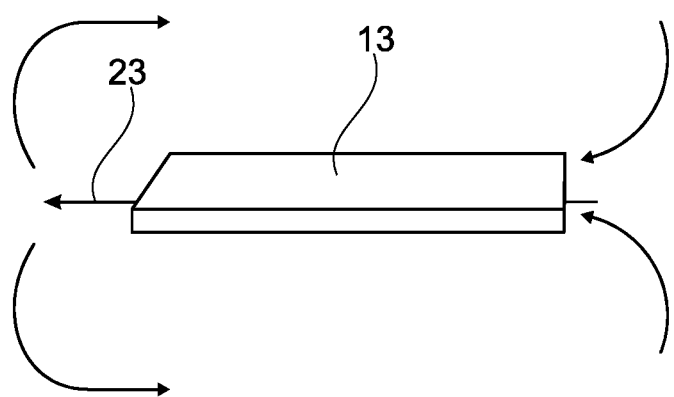
Figure 6:
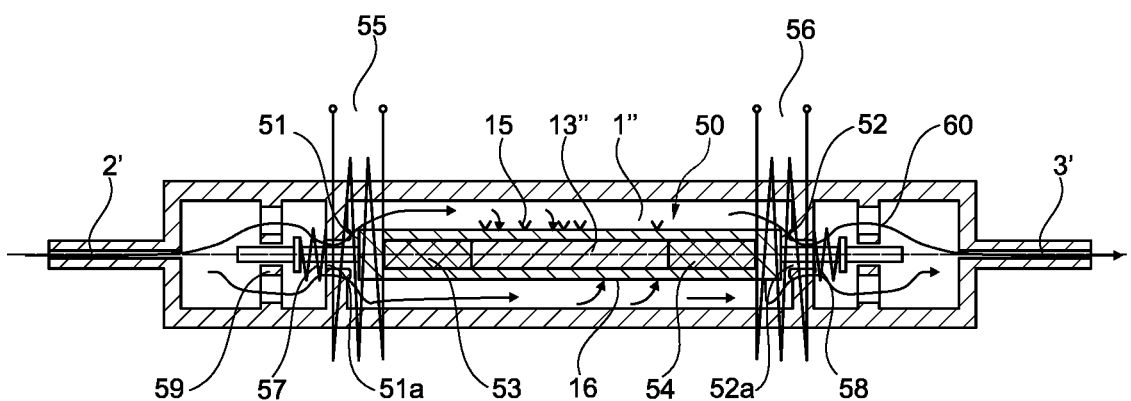
Figure 7:
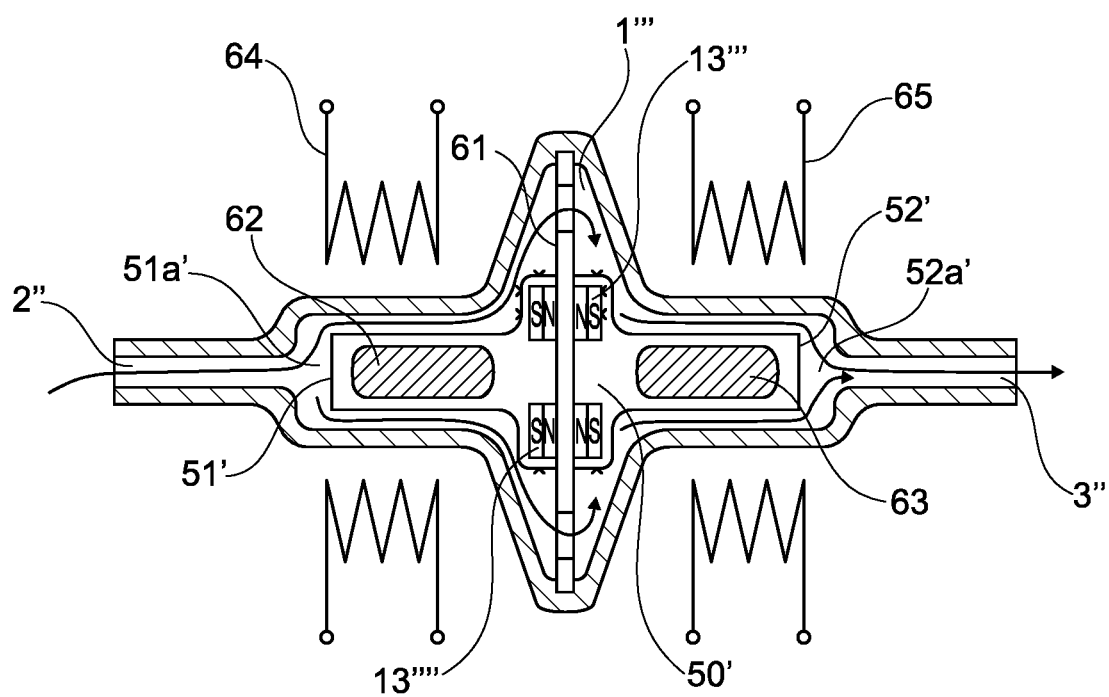
Figure 8:
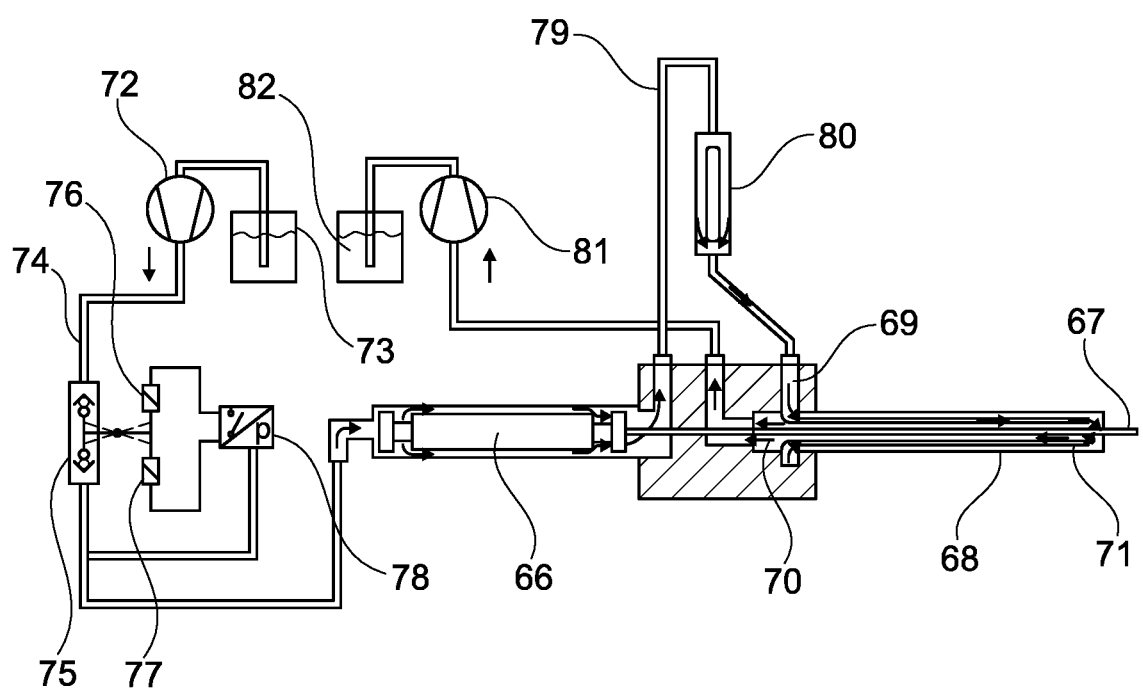
Figure 9:
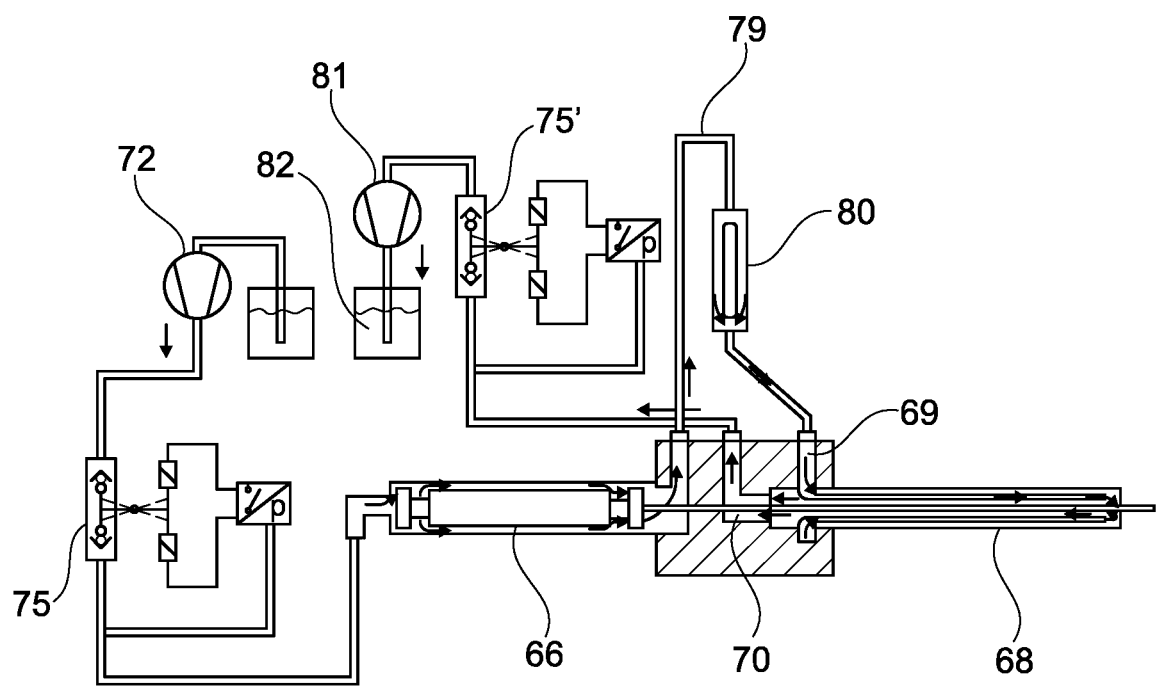
Figure 10:
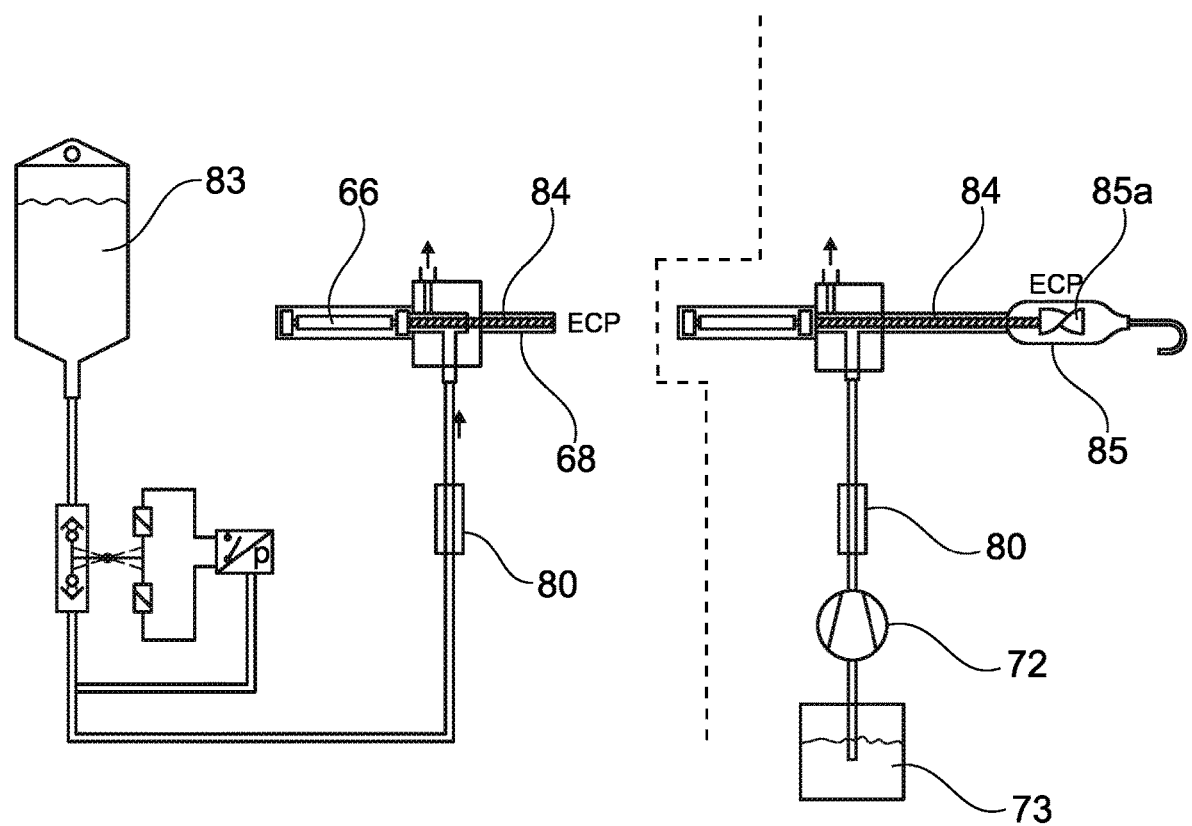
Figure 11:
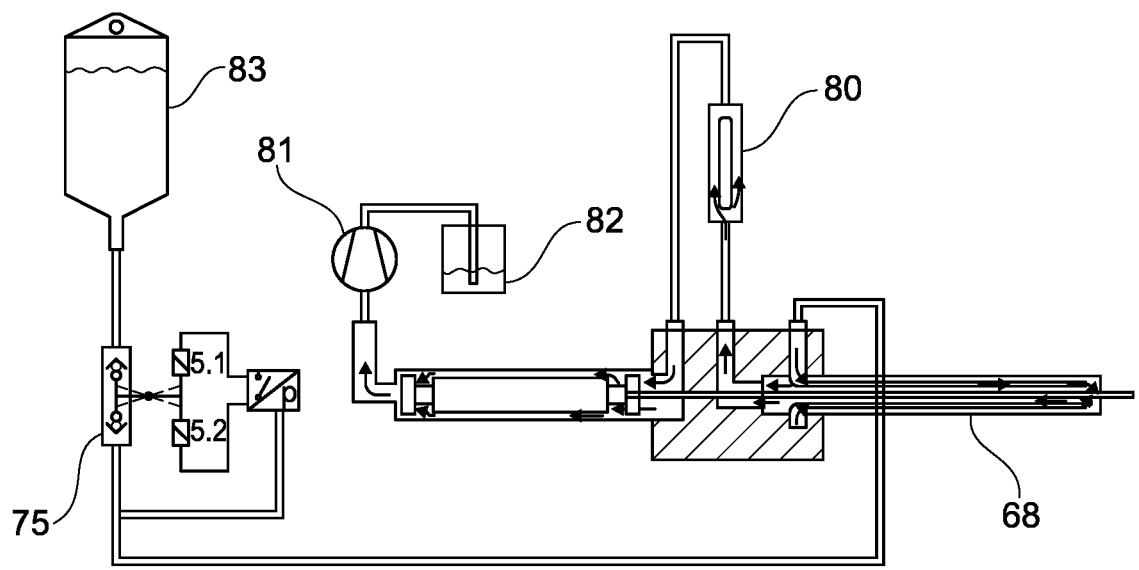
Figure 12:
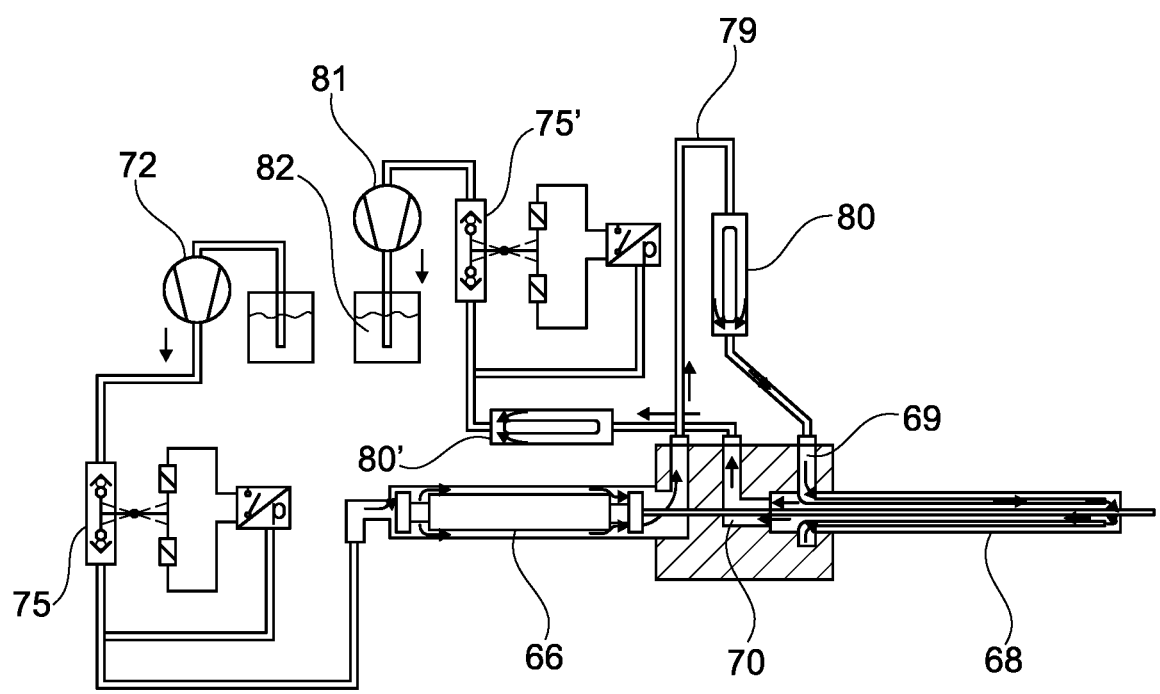

Thereby Are Shown In:

FIG. 1 in a longitudinal section, a separating device with a transport channel which is designed as a fluid channel and in which fluid flows around a magnet, FIG. 2 a catheter device with a rotating shaft and with a separating device, in a longitudinal section, FIG. 3 a cross section of the device which is shown in FIG. 2, FIG. 4 a magnet device, with which the magnet around which fluid flows is magnetised transversely to the longitudinal direction of the fluid channel, FIG. 5 a magnet which is magnetised in its longitudinal direction and in the longitudinal direction of the fluid channel, FIG. 6 a valve which is connected to a separating device, FIG. 7 a further valve which is connected to a separating device, FIG. 8 a drive unit for a functional element which can be driven by way of a shaft rotating in a catheter, FIG. 9 a modification of a drive unit according to FIG. 8, FIG. 10 and FIG. 11 in each case, further designs of drive devices for a shafts rotating in a catheter as well as FIG. 12 a modification of a drive unit according to FIG. 9.

FIG. 1 in a longitudinal section shows a transport channel 1 which is designed directly as a fluid channel, and leads a fluid, for example in the form of a saline solution. The fluid at a feed opening 2 enters into the transport channel 1 and exits out of this at the discharge opening 3. The flow directions are indicated by arrows 4, 5, 6. A holder 7 for a magnet device is provided at the end of the transport channel 1 which is situated upstream, whereas a further holder 8 for a magnet device is provided at the end which is situated downstream. The holders 7, 8 can be designed as star holders with fluid through-openings 9, 10. The cross section of the through-openings 9, 10 should thereby be so large that the holders 7, 8 represent no significant flow resistance to the liquid.

The feed opening 2 just as the discharge opening 3 can be connected in each case to a catheter, which for example can be pushed onto a connection piece 11, 12.

A magnet device with a permanent magnet 13 which is surrounded on all sides by an encasing 14 protecting the magnet from the influence of the corrosive fluid is arranged in the inside of the transport channel. The encasing can for example be a designed as a plastic encasing, a coating or also be designed as a metallisation, which is to say a metallic coating of a noble metal.

The flow of the fluid through the transport channel 1 will not be a strictly laminar flow, but will have certain turbulence or eddies. In any case, the particles 15, 16 which as magnetic particles are present in the fluid circuit for example due to the wearing of magnetic parts are attracted to certain regions of the magnet. By way of additional eddy elements in the transport channel 1, one can also ensure that the flow of the fluid is eddied, so that the probability of particles transported in the fluid getting into the proximity of the magnet is increased. The term "magnetic particles" thereby is to be understood as all particles which are attracted by a magnet, in particular, but not only ferromagnetic particles.

If the particles once get into a capture region of the magnet, then they are firmly held there and are held back from the fluid flow. The spearing device which is shown in FIG. 1 can be used as a disposable separating device for example, and be disposed of after use. The separated metal particles 15, 16 can remain on the magnet 13 in this case. One can also envisage the magnet 13 being designed as an electromagnet or being magnetised by a magnetising device from outside the transport channel. In both these cases, the magnetisation of the magnet 13 can be temporarily lifted, in order to rinse the transport channel and the outer surface of the magnet 13, 14 and to remove the magnetic particles 15, 16. In this case for example, another catheter can be connected to the connection piece 12, and this leads the fluid used for rising together with the particles into a capture container.

The magnet 13" as is shown in FIG. 4 in more detail, can be magnetised for example by way of an external magnetisation device 17 with an electromagnet part 18 as well as pole shoes 19, 20, so that its magnetisation direction runs along the arrows 21, 22 which are shown in FIG. 4, transversely to the longitudinal direction of the transport channel (assuming that the magnet represented in FIG. 4 is used for a device as is represented in FIG. 1). The electromagnet 18 can then be simply switched off for rinsing or its effect can be at least partly reversed, in order to overcome the residual magnetisation of the magnet 13.

A further constructional form of a magnet is represented in FIG. 5, wherein its outer geometric shape corresponds to that of the magnet represented in FIG. 1, wherein the magnetisation, indicated by the arrow 23, runs in the longitudinal direction of the magnet 13.

Metallic particles with the use of such a magnet would tend to collect rather at the two axial ends than on the longitudinal sides as with a magnet magnetised transversely to the longitudinal direction and represented in FIG. 4.

FIG. 2 shows a catheter device with a catheter 24, in which a rotating metallic shaft 25 is guided. A catheter holder which comprises a transport channel 1' is indicated with the reference numeral 26 in FIG. 2. The reference numeral 27 indicates a housing which surrounds the catheter holder 26 and forms a ring body comprising a cavity, in which a magnet 13' is arranged. The shaft 25 exits the catheter 24 within the housing 27. The catheter 24 exits from the catheter holder 26 or ends at one end of the catheter holder 26. In any case, the fluid which is located in the catheter 24 and which flows slowly along the shaft 25 as a rinsing and lubricating fluid can enter into a fluid channel 28 which is formed at the end of the catheter 24 and which has a significantly larger cross section than the free cross section of the catheter 24 which is already reduced by the shaft 25 which is led in this. The fluid channel 28 is located upstream of a mechanical bearing 29 which can be designed as a plain bearing, and in the direct region of influence of the magnet 13'. The magnet 13' is designed as a permanent magnet but can however also be designed as an electromagnet.

The magnetic particles 30 in the region of the fluid channel 28 collect on the wall of the channel which faces the magnet 13'. The magnetic particles are held back from the fluid in this manner and do not get to the bearing 29.

The further course of the shaft 25 is not represented, but further mechanically functioning parts, such as for example pumps or millers which are driven by a shaft and which must be protected from the influence of the magnetic particles, can be provided distally of the connection coupling in the further course. The housing 27 apart from the catheter holder 26 yet accommodates a rinsing device with connection pieces 32, 33 for a rinsing fluid, in order to rinse the catheter 24.

The magnet 13' can be withdrawn from the housing 27 so as to remove the captured magnetic particles 30, so that the magnetic particles can then be rinsed away. This should be effected outside the operating time of the shaft and the respective bearings and functional elements, in order to take care of these. If with regard to the magnet 13' it is the case of an electromagnet, then this can be simply temporarily switched off for the rinsing.

A cross section through the catheter arrangement of FIG. 2 is shown in FIG. 3, with the housing 27, the transport channel 28 in the region behind the end of the catheter 24 as well as the magnet 13' which is located in a cavity of the housing 27.

FIG. 6 shows a magnet valve with a transport channel 1", through which a fluid flows between a feed opening 2' and a discharge opening 3'. A closure body 50 can be driven within the transport channel 1" between a first closure position and a second closure position, wherein a first closure surface 51 closes a valve opening 51a in the first closure position, whereas a closure surface 52 closes a valve opening 52a in the second closure position.

Two armature bodies 53, 54 are integrated into the closure body 50 and are drivable by the magnetic field of two valve drive coils 55, 56. The magnet 13" of the separating device is arranged axially between the armature bodies 53, 54, in a manner aligned manner to these. The armature bodies with the magnet body 13" are provided with a common solid matter encasing.

Holding springs 57, 58, in the absence of an excitation of the valve drive coils hold the closure body in a middle position, in which the valve is opened. Two plain bearings 59, 60 are provided at the ends of the valve housing for guiding the closure body 50.

FIG. 7 shows a valve with a feed opening 2"', with a discharge opening 3"' and with a closure body 50'. The closure body 50' is can be driven within the transport channel 1" between a first closure position and a second closure position, wherein a first closure surface 51' closes a valve opening 51a' in the first closure position, whereas a closure surface 52' closes a valve opening 52a' in the second closure position. The closure body 50' is mounted in the housing of the valve by way of an elastic, permeable disc 61 and is held in an opened middle position. The disc 61 carries separating magnets 13"', 13"" which are connected in the closure body 50' to valve drive armatures 62, 63 and together with these are encased by a protective layer.

The valve drive armatures 62, 63 are drivable in the field of the coils 64, 65. Particles in the transport channel can settle on the separating magnets on the protective layer and are firmly held there.

FIG. 8 shows a drive device with a drive armature 66 which can be driven in rotation and which drives a rotating shaft 67 in a catheter 68. A feed channel 69 is arranged radially to the outside, and a return channel 70 is arranged radially to the inside, in a manner concentrically to one another within the catheter 68, and arranged to the outer envelope of the catheter. The feed channel 69 and the return channel 70 are separated from one another by a hose-like separating wall 71.

A rinsing fluid is pumped from a reservoir 73 through a cannula 74 and a valve 75 by way of a volume-controlled peristaltic pump 72. Two magnets 76 and 77 serve for the drive of the valve and are activated by way of a pressure switch 78 with the aim of maintaining a constant pressure in the feed channel 69. The fluid for this is led through the valve 75 and through the housing of the drive armature 66, through the transport channel 9 and through the separating device 80 where particles are actively filtered out of the fluid. The separating device 80 can be constructed as with the separating device shown in FIG. 1. From there, the fluid flows into the catheter 68 radially outwards through the feed channel 69 and radially inwards through the return channel 70, as well as from there to a peristaltic pump 81 which sucks the fluid and leads into the reservoir 82. The peristaltic pump 81 however can also serve for back-rinsing and for this purpose can be operated in a manner such that it delivers the fluid to the return channel 70 and from there via the feed channel 69, through the separating device back to the valve 75 into the reservoir 73, in order for example to remove the captured particles from the separating device.

FIG. 9 shows a construction similar to that of FIG. 8, wherein additionally to the valve 75, a second valve 75' is arranged between the return channel 70 and the return pump 80, in front of the drive armature 66 and behind the peristaltic pump 72. Whilst FIG. 8 is applied with rinsing systems, in which no undesired vacuum is produced in the return due to installation components, it is possible to apply FIG. 9 also with rinsing systems, in which an undesired vacuum arises in the return (e.g. due to the winding direction of the flexible shaft). This vacuum is recognised by the sensor which then, by way of closing the valve 75' to the bottom, ensures that no medium gets out of the container 82 via the pump 81 into the rinsing circuit. The separating device is thus arranged between two valves and also between two fluid delivery devices, of which at least one, in particular both, can be switched over with respect to the delivery direction of the fluid, in order to reverse the flow direction.

With regard to the construction according to FIG. 10, in comparison to the construction in FIG. 8, only a peristaltic pump 72 is replaced by a reservoir 83 which permits a gravity flushing, by way of the fluid flowing through the valve 75 and further to the catheter 68 due to gravity. The rotating shaft 84 within the catheter 68, due to its stranded/twisted construction based on twisted strands has a helical (coiled) outer structure, which on rotation gives this itself a pumping effect in the direction away from the drive armature 66. Another variant with a volume-controlled peristaltic pump 72 and with a reservoir 73 is represented on the right side of FIG. 10, to the right of the dashed line, for the feed of fluid to the catheter 68. The peristaltic pump there delivers the fluid to the inside of the catheter which for example is introduced into the body of a patient and there ends at a heart pump 85 with a rotor 85a. The heart pump for example can be radially compressed which is to say as a whole can be particularly prone to particles which get therein. The fluid then flows back from there. A separating device 80 can be provided in each case upstream of the catheter 68 in the flow direction, between this and the delivery device 73, 83, in particular in any case upstream of the heart pump 85.

FIG. 11 shows a constellation similar to that of FIG. 9, wherein a gravity delivery 83 is envisaged instead of the peristaltic pump 72, wherein on normal operation, fluid leads from there via the valve into the catheter 68 and there firstly radially outwards through the feed channel 69, radially inwards into the return channel 70 as well as from there to a peristaltic pump 81 which sucks the fluid and leads into the reservoir 82. The fluid, between the return channel 70 and the peristaltic pump 81 firstly passes the separating device 80 which is arranged between the return channel and the housing of the drive armature 66. The fluid thereafter flows past the drive armature 66 to the peristaltic pump 81. The mounting of the drive armature can be relatively insensitive, so that the through-flow direction of the fluid there is of minor significance. What is important is that that the housing of the drive armature is supplied with fluid to ensure a good lubrication. The selected arrangement moreover ensures that magnetic wear particles of the rotating shaft 84 in this case cannot damage the bearings of the drive armature.

FIG. 12 shows a construction similar to FIG. 9, wherein a further separating device 80' ensures that the function of the sealing surfaces of the valve 75' is not compromised by clinging particles.

The invention, in particular with medical applications, but also with other applications, permits magnetic particles to be held back from a fluid flow with the help of magnet devices, wherein the magnets of the magnet devices are protected from the corrosive effects of the fluid.

The catheter device according to the invention can be combined with all separating devices which are represented here, thus for example separating devices according to one of the aspects 1 to 11 which are specified below and/or further separating device according to the description of the figures and the current patent claims. For this, it is also possible to not only provided one, but also several separating devices per catheter device.

With respect to the separating devices, in particular, the following aspects apply:

1. A separating device for holding back magnetic particles which are located in a fluid, with a transport channel, in which the fluid can be moved in a throughflow direction, and with a magnet device, wherein the magnet device comprises at least one magnet which is separated from the fluid by a magnetically permeable solid matter layer.

2. A separating device according to aspect 1, characterised in that the magnet exclusively interacts with magnetic or magnetisable particles in the fluid in the transport channel.

3. A separating device according to aspect 1 or 2, characterised by
a first and a second fluid connection, between which the separating device forms a fluid-tight fluid channel.

4. A separating device according to aspect 1, 2 or 3, characterised in that
a magnet which is enveloped by a magnetically permeable solid matter layer and around which fluid can flow on all sides, is arranged in the fluid channel.

5. A separating device according to aspect 4, characterised in that
the magnet is designed as a cylinder or cuboid, whose length in the longitudinal direction of the fluid channel is larger than its diameter, and which is arranged in a cylindrical section of the fluid channel.

6. A separating device according to aspect 5, characterised in that
the magnetic field lines run within the magnet, transversely, in particular perpendicularly to the flow direction of the fluid.

7. A separating device according to aspect 4, characterised in that
the magnet in the throughflow direction has a smaller extension than perpendicular to the throughflow direction.

8. A separating device according to aspect 1, 2 or 3, characterised by
a ring body which surrounds the transport channel, wherein the transport channel is configured to receive a catheter with a throughflow channel, and wherein a magnet is arranged in the ring body, in a cavity situated next to the transport channel.

9. A separating device according to aspect 8, characterised in that
the ring body is designed as one piece in the peripheral direction.

10. A separating device according to aspect 8, characterised in that
the ring body in the peripheral direction is interrupted at least once and in particular can be folded open for sticking onto a catheter.

11. A separating device according to aspect 1 or one of the following, characterised in that
the flow channel in the region of the magnet device has a larger cross section than in a region which in the flow direction of the fluid is arranged upstream of the region of the magnet device.

12. A catheter device with a catheter, in which a rotating shaft consisting at least partly of a magnetic material is arranged, and with a separating device which comprises a ring body which surrounds the rotating shaft and is with a cavity containing a magnet body, wherein the magnet body with respect to the flow direction of the fluid through the catheter is arranged downstream of a location, at which the shaft exits out of the catheter surrounding it.

13. A protective device for a functional element, which is in connection with a flowing fluid, characterised in that a separating device for holding back particles located in the fluid and with at least one magnet element, in particular a separating device according to one of the aspects 1 to 11, is provided along a flow channel for the fluid, in particular a catheter, in a manner distanced to the functional element and in particular separated from it.

14. A catheter system comprising a separating device according to one of the aspects 1 to 11, and/or a protective device according to aspect 13, characterised in that at least one electrical element for the control of the functional element and/or for the magnet control can be separated from the remaining catheter system.

The invention claimed is:

1. A catheter device for holding back magnetic particles which are located in a fluid comprising:
a fluid transport channel, wherein fluid can be moved through the fluid transport channel in a throughflow direction and wherein the fluid transport channel comprises a reservoir for an intermediate storage of particles, wherein the reservoir is magnetically influenced such that metallic particles remain in the reservoir even when the fluid transport channel is subjected to throughflow; and
a magnetic separation device arranged with the fluid transport channel, wherein the magnetic separation device comprises at least one magnet which is separated from the fluid by a magnetically permeable solid matter layer.

2. A catheter device according to claim 1, wherein the at least one magnet interacts exclusively with magnetic or magnetisable particles in the fluid in the fluid transport channel.

3. A catheter device according to claim 1, wherein the at least one magnet is enveloped by the magnetically permeable solid matter layer and is arranged in the fluid transport channel such that fluid in the fluid transport channel will flow around the at least one magnet enveloped by the magnetically permeable solid matter layer.

4. A catheter device according to claim 3, wherein the at least one magnet is designed as a cylinder having a length in a longitudinal direction of the fluid transport channel that is larger than a diameter of the cylinder, and which is arranged in a cylindrical section of the fluid transport channel.

5. A catheter device according to claim 4, wherein magnetic field lines within the at least one magnet run transversely to a flow direction of the fluid in the fluid transport channel.

6. A catheter device according to claim 4, wherein magnetic field lines within the at least one magnet run perpendicularly to the flow direction of the fluid.

7. A catheter device according to claim 3, wherein the at least one magnet in the throughflow direction has a smaller extension than perpendicularly to the throughflow direction.

8. A catheter device according to claim 3, wherein the at least one magnet is designed as a cuboid having a length in the longitudinal direction of the fluid transport channel that is larger than a diameter of the cuboid, and wherein the cuboid is arranged in a cylindrical section of the fluid transport channel.

9. A catheter device according to claim 1 wherein a ring body surrounds the fluid transport channel, wherein the fluid transport channel is configured for receiving a catheter with a throughflow channel, and wherein the at least one magnet is arranged in the ring body in a cavity situated next to the fluid transport channel.

10. A catheter device according to claim 9, wherein the ring body is designed as one piece in the peripheral direction.

11. A catheter device according to claim 9, wherein the ring body is interrupted at least once in the peripheral direction.

12. A catheter device according to claim 11, wherein the ring body can be folded open for sticking onto a catheter.

13. A catheter device according to claim 1, wherein the reservoir comprises two ends, wherein both are connected in a fluid-conducting manner to the fluid transport channel.

14. A catheter device according to claim 1, wherein the reservoir is designed as a cross-sectional enlargement of the fluid transport channel which is spatially delimited.

15. A catheter device for holding back magnetic particles which are located in a fluid comprising:
   a fluid transport channel, wherein fluid can be moved through the fluid transport channel in a throughflow direction and wherein the fluid transport channel comprises a reservoir for an intermediate storage of particles, wherein the reservoir comprises two ends, wherein both are connected in a fluid-conducting manner to the fluid transport channel; and
   a magnetic separation device arranged with the fluid transport channel, wherein the magnetic separation device comprises at least one magnet which is separated from the fluid by a magnetically permeable solid matter layer.

16. A catheter device for holding back magnetic particles which are located in a fluid comprising:
   a fluid transport channel, wherein fluid can be moved through the fluid transport channel in a throughflow direction and wherein the fluid transport channel comprises a reservoir for an intermediate storage of particles, wherein the reservoir is designed as a cross-sectional enlargement of the fluid transport channel which is spatially delimited; and
   a magnetic separation device arranged with the fluid transport channel, wherein the magnetic separation device comprises at least one magnet which is separated from the fluid by a magnetically permeable solid matter layer.

* * * * *